United States Patent [19]

Isaacson

[11] Patent Number: 4,479,495

[45] Date of Patent: Oct. 30, 1984

[54] ACUPRESSURE POINT STIMULATOR DEVICE

[76] Inventor: Gary S. Isaacson, 1827 Haigt St., Suite 2, San Francisco, Calif. 94117

[21] Appl. No.: 424,573

[22] Filed: Sep. 27, 1982

[51] Int. Cl.³ .................... A61B 17/12; A61B 17/34
[52] U.S. Cl. .................................. 128/327; 128/329 A
[58] Field of Search ........... 128/329 A, 303 R, 95–99, 128/327, 1.3

[56] References Cited

U.S. PATENT DOCUMENTS

| | | | |
|---|---|---|---|
| 4,162,672 | 7/1979 | Yazaki | 128/1.3 |
| 4,182,338 | 1/1980 | Stanulis | 128/329 A |
| 4,273,130 | 6/1981 | Simpson | 128/329 A |
| 4,308,861 | 1/1982 | Kelly | 128/68 |
| 4,319,574 | 3/1982 | Sun et al. | 128/303 R |
| 4,391,270 | 7/1983 | Uragami | 128/1.3 |

*Primary Examiner*—C. Fred Rosenbaum
*Assistant Examiner*—C. W. Shedd
*Attorney, Agent, or Firm*—David Pressman

[57] ABSTRACT

An acupressure device for applying pressure to specific points on a human body comprises a stimulator (14) which is attached to a flexible cinching strap or band (10) of a length sufficient to extend circumferentially around a body part, including a releasable connecting means to facilitate the positioning and securing of the terminus of the stimulator against a specific point on the human body. The stimulator has a convex curved side (26) which is attached to the flexible strap. Opposite the curved side and extending therefrom, an elongated protuberance (20) extends and terminates in a blunt or pointed surface end (22). This end can be made to contact and apply pressure to a selected point on the user's body by extending the strap around a portion of the body and tightening same with the terminus of the stimulator in proper position.

16 Claims, 12 Drawing Figures

ACUPRESSURE POINT STIMULATOR DEVICE

BACKGROUND

1. Field of Invention

This invention relates in general to the stimulation of specific points on the human body and in particular to the treatment of disorders by the application of pressure to selected and specific locales on the body.

2. Prior Art

The treatment of physiological disorders by means of acupuncture is well known. Acupuncture is the method of employing insertion of needles into the skin at exact, spatially defined points in order to treat specific disorders.

One problem which has been noted with acupuncture is that a skilled practitioner is generally required to administer the treatment. Another disadvantage of acupuncture techniques is because the skin is that punctured with the acupuncture needle, a danger of infection is present.

Akin to acunpuncture is acupressure, the application of pressure at the traditional acupuncture points. Acupressure is frequently employed in lieu of acupuncture.

The traditional theory of acupuncture and its delineation of point locations are identical in acupressure, the only difference being that in acupressure, only pressure is applied to the selected points. While this pressure is not sufficient to puncture the skin, it still is an effective treatment for certain disorders. In this regard see *Acupressure: Acupuncture Without Needles*, J. V. Cerney, Cornerstone Library, New York, 1974, or *Acupuncture Therapy*, p. 100, Mary Austin, ASI Publishers, New York, 1980.

For this reason, the terms "acupuncture point," and "acupressure point" are used interchangeably to denote an identical and specific body point. The term "acupoint" also may be used to denote these body points. Since the vast majority of the traditional literature on the subject of acupoints relates to the practice of acupuncture, most acupressure theory is simply transposed or extrapolated from this greater and older school of knowledge.

One notable difference between acupuncture and acupressure is that acupressure, by virtue of its lack of puncturing the skin, relieves muscular tension while also contacting the traditional energy pathways of acupuncture.

For example, one acupressure device, shown in U.S. Pat. No. 4,319,574 to Sun and Sun, 1982, is arranged to apply pressure to points on the external ear, thereby employing an acupuncture specialty known as auricular therapy. However, the disadvantage of this device is that it is mainly useable on the ear only, and not at most other acupoints on the body. Particularly, it is not applicable to the most effective acupoints, which are located on the limbs, specifically the areas between the knees and toes and the areas between the elbows and fingertips.

Also, the traditional literature of acupuncture often specifies various angles of insertion of needles to effectively stimulate a given acupoint for respective therapeutic results. Likewise, in acupressure, pressure is applied at various angles at a given acupoint for differing therapeutic considerations. In this regard see *Essentials of Chinese Acupuncture*, Foreign Languages Press, Beijing, 1980, or *Acupuncture: A Comprehensive Text*, Shanghai College of Traditional Medicine, translated and edited by J. O'Connor and D. Bensky, Eastland Press, Chicago, 1981.

Furthermore, in many cases, palpable muscular tension accumulates at or around acupoints. Experience has shown that the application of pressure, steadily or variably applied, tends to release or dissipate this tension. In many cases, variably applied pressure has an advantage in that it is less traumatic and generally more comfortable for the recipient. In this regard see *Acupressure Way of Health*, Iona Teeguarden, Japan Publications, Tokyo, 1978.

Also, points of muscular tension may shift, necessitating differing angles of contact at or directly adjacent to the exact locale of an acupoint to make contact properly with the foci of greatest tension.

Another acupressure device which I have seen comprises a orb-shaped metal stimulator attached to a retaining band. This device, intended for an acupoint near the wrist, provides pressure in a direction limited and restricted by circumferential or lateral force imparted to the stimulator as the band is tightened. The disadvantage of this device is that the angle of contact of the orb to the skin does not provide proper or optimum pressure on the acupoint which it is intended to stimulate. The acupoint for which this device is intended is known in traditional literature as Pericardium 6, or the Chinese appellation Neiguan. Most references recommend that this point be stimulated perpendicularly. In this regard see *Essentials of Chinese Acupuncture* or *Acupuncture: A Comprehensive Text*. However, the lateral force upon the metal stimulator imparted by the strap results in the acupoint being inappropriately and inadequately contacted, if at all. Moreover, the perpendicular pressure which is present is reduced because of the inefficient lateral force imparted. Further, since the place of attachment of the orb to the strap is flat, additional skewing or undesirable, inefficient lateral force results.

Lastly, both this device and the aforementioned Sun and Sun device provide minimal or no motion to help dissipate the tension at or adjacent to an acupoint.

OBJECTS

It is accordingly one object of my invention to provide a device which is designed such that pressure may be applied to a selected point on the body by the user on a frequent basis without the assistance of a medical or acupuncture or acupressure practitioner. Another object is to provide a device which is useful for the application of varying degrees of pressure to an acupoint, the exact amount of pressure to be determined by the user and readily adjustable throughout the range from no pressure to heavy pressure.

Further objects are to provide an acupressure device which does not puncture the skin; is capable of applying pressure to selected regions of the body, especially but not exclusively, the limbs, for the treatment of various disorders; can be worn on one's body unobtrusively; can be easily concealed under regular clothing; and need not impair the user's regular activities in any way.

A still further object is to provide a device which can apply pressure at a range of angles, from acute to perpendicular, such that acupoints which would otherwise be difficult to contact properly can be effectively stimulated. This variability of angle of contact makes possible the effective stimulation of body points located, for example, behind a bone. One such point, known in traditional literature as Spleen Six, or the Chinese appellation Sanyinjiao, is located on the posterior margin of the tibia approximately three inches directly above the medial malleolus of the ankle. Dr. Mary Austin, in *Acupuncture Therapy*, calls this point one of the "Great Points of Chinese Acupuncture." Because of its location and prominence, this particular acupoint will be used herein for illustrative purposes.

Yet further objects are to be able to vary the angle of contact of an acupressure device with the acupoint, to provide a device which may apply varying motion, in addition to pressure to a specific acupoint in a cam-like manner, such that it is able to provide a rocking or reciprocating back-and-forth contact, in response to the motion imparted by the normal muscular contractions and expansions involved in a regular human movement—for example, walking.

A yet further object is to provide an acupressure device which is useful for the application of pressure, with or without motion, to various regions of the body and yet which is easily removed when desired.

Further objects and advantages of my invention will become apparent from a consideration of the drawings and ensuing description thereof.

DRAWINGS

Figures 3, 3A, 3B, 3C, 3D, 3E:
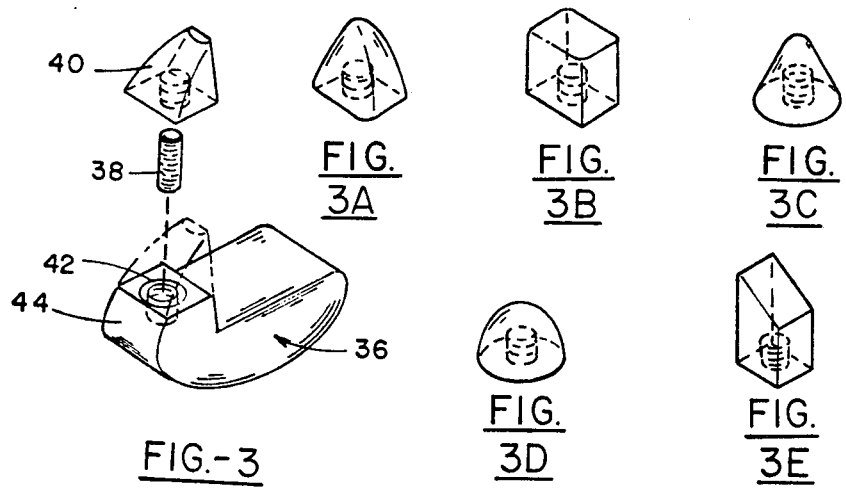
FIG. 3 is an exploded isometric view of another embodiment of the stimulator of the present invention.

FIGS. 3A, 3B, 3C, 3D, and 3E are partial sectional views of various possible embodiments of a portion of the device shown in FIG. 3.

Figures 4, 5:
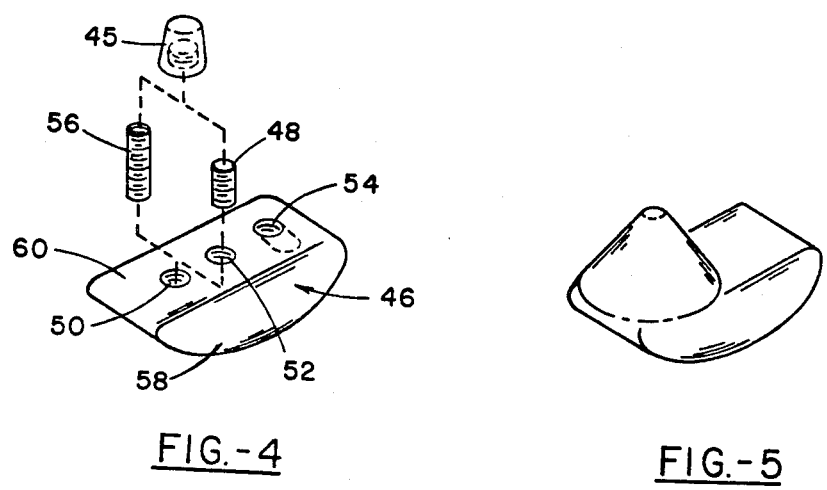

FIG. 4 is an exploded isometric view of another embodiment of the stimulator of the present invention.

FIG. 5 is an isometric view of another embodiment of the stimulator of the present invention.

Figure 6:
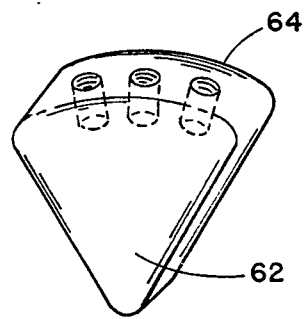

FIG. 6 is an isometric view of still another possible embodiment of the stimulator of the present invention.

Figure 7:
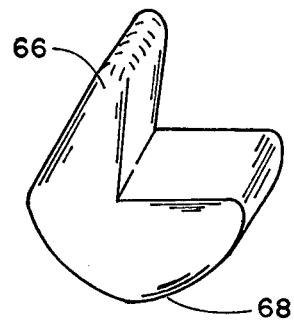

FIG. 7 is an isometric view of still another embodiment of the stimulator of the present invention.

REFERENCE NUMERALS

10. Strap or band
12. Rectangular ring
14. Stimulator
16. Screw
18. Threaded hole or female insert
20. Cusp
22. Top of cusp
24. Base portion of stimulator
26. Bottom surface of stimulator
28. Flat side of base of stimulator
30. Edge of Stimulator
32. Side of cusp
36. Stimulator FIG. 3
38. Threaded Shaft
40. Tip
42. Hole in 44
44. Base of cusp
45. Tip of FIG. 4
46. Stimulator of FIG. 4
48. Stud
50. Hole
52. Hole
54. Hole
56. Long stud
58. Base
60. Flat upper surface
62. Cusp FIG. 6
64. Base FIG. 6
66. Long cusp FIG. 7
68. Curved Surface

FIG. 1—DESCRIPTION

Figure 1:
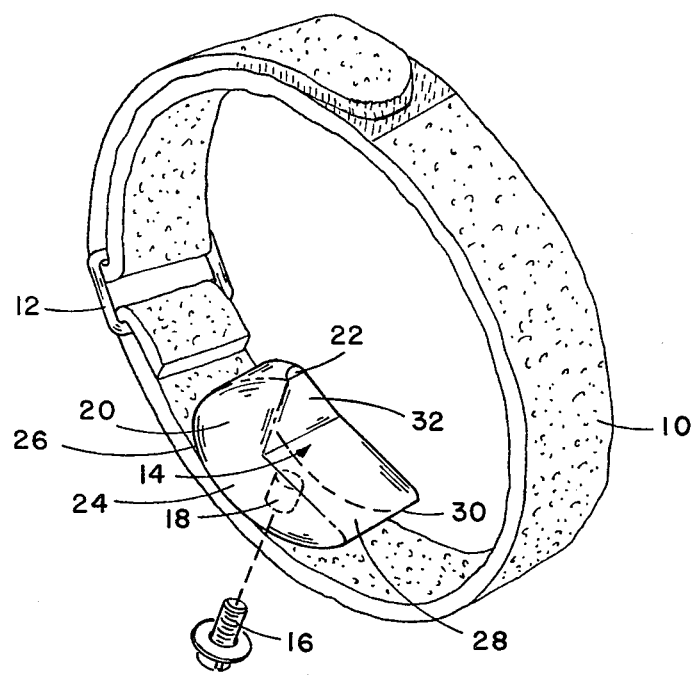
FIG. 1 is an isometric view of one embodiment of the present invention showing a stimulator attached to a flexible band or cinching strap.

FIG. 1 shows a first embodiment of a device for stimulating a body point. The device comprises a flaccid or flexible band or cinching strap 10 which is preferably made of a flexible material such as cloth, nylon, elastic, etc. or any combination thereof. Band 10 includes a rectangular ring-type buckle 12 around which the strap is folded back and attached to itself to facilitate tightening the strap to the desired tautness by the user. A hook and pile fastening system (e.g., Velcro brand) is preferred because it facilitates greater flexibility, ease of use, and because the attachment points are continuous and need not be predetermined by the placement of holes, as in a pivoting-tongue apparatus. This tightening mechanism may be replaced or augmented by a buckle and pivoting-tongue arrangement (not shown), as in a conventional watch strap.

In a preferred embodiment, the band or strap is also made elastic so as to accomodate any motion or oscillation of the stimulator as it is worn by the active user. The elastic characteristics also facilitate ease of use and application for the wearer.

Figure 2:
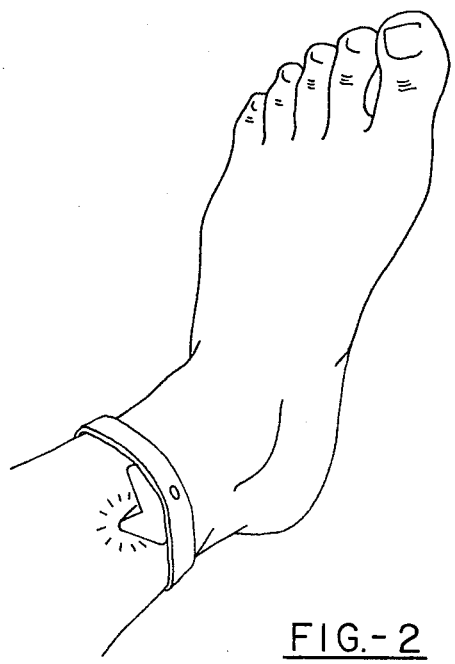
FIG. 2 shows the device in place on user's leg stimulating the approximate locale of the acupoint known as Spleen Six.

A stimulator 14 is attached to band 10 and may be comprised of a rigid or sem-rigid material or any combination thereof. Preferably the tip of the stimulator is made of rubber, foam, or similar material, i.e., silicone, latex, or urethane, which has characteristics of plasticity, pliability, and compressability. Stimulator is attached to strap 10 by a screw 16 which extends through strap 10 into a hole tapped directly in a symmetrical location (the center) of the back side of stimulator 14 or into a threaded female insert 18 imbedded in stimulator 14. Screw attachment 16 is preferred because it facilitates easy removal of stimulator 14 from band 10 so the band can be easily cleaned or laundered as the need arises. When in use, as shown in FIGS. 1 and 2, band 10 forms a loop which extends around a portion of an animal's body and stimulator 14 so as to hold stimulator 14 against such portion of the animal's body. Thus in use band 10 forms a loop which is parallel to an imaginary plane.

Stimulator 14 comprises a base portion 24 having a convex bottom surface 26 adjacent band 10 and a generally flat top surface 28 opposite surface 26, except for a protruding cusp portion 20 which extends up from surface 28 from one side thereof. Thus top surface 28 has a generally lower (flat) portion and a protruding or cusp portion 20. Bottom surface 26 and one lateral side of top surface 28 taper together to form an edge 30. At the other lateral side of stimulator 14, bottom surface 26 curves up and around to form the distal convex side of cusp 20, terminating at top surface 22. The other sides of stimulator 14 are flat and parallel for base portion 24 and taper together to form opposing side walls of cusp 20, which terminates at top surface 22. Cusp 20 also has a side 32 extending up from surface 28 of base 24 at a slightly obtuse angle, but it will be understood that right and acute angular relationships are feasible; an acute angular relationship is shown in FIG. 7. Cusp 20 terminates in a blunt top surface 22, which is the actual contact point between stimulator 14 and the acupoint on the user's body.

Blunt surface 22 is shown as planar but may also have a rounded, convex shape. However it is essential that surface 22 be sufficiently blunt that the skin is not pierced or punctured when the band is tightened while positioned on the user.

The thickness of one preferred embodiment of stimulator 14 (between the flat sides thereof) is 25.4 mm, the height of base portion 24 (from the portion of bottom 26 in contact with strap 10 to flat surface 28) is 12 mm, the height of cusp 20 30 mm, and the width (from edge 30 to the opposite side) 36 mm.

The area of the blunt terminus 22 is approximately 2 sq mm, but may vary down to a size approximating a typewritten period to a comparatively much larger surface, approximating the size of a large fingertip, an area of about 40 sq. mm. The concave-shaped back of the stimulator, the portion upon which the cinching strap attaches, may vary from a true radius of a circle to an irregular curved, elliptical, parabolic, hyperbolic, or airstream-shaped curve. Also, the angle of the protuberance relative to the side opposite the curved surface may be varied to facilitate more effective contact of various acupoints.

Muscular tension seems to accumulate at and around an acupoint and often, the degree of sensitivity which a person experiences when a specific acupoint is stimulated tends to be in direct proportion to the extent of the problem or disorder being treated. Also, as the tension changes at an acupoint, other tips may be preferable. Therefore, varying sizes, configurations, and hardnesses for the blunt terminus of cusp 20 are provided.

FIG. 2—DESCRIPTION

FIG. 2 shows my invention in place on the leg stimulating the approximate locale of the acupoint known in traditional literature as Spleen Six.

FIGS. 3 AND 3A TO 3E—DESCRIPTION

In order to provide cusps of various sizes, shapes, and hardnesses to increase comfort and ease of use to the user, the embodiment of stimulator 36 of FIG. 3 is provided. Here the terminus of the cusp is removable and different tips of various characteristics may be interchanged. This variability is facilitated by a threaded shaft or pin 38 which mates with a female threaded portion in terminus or tip 40 and with a similar threaded hole 42, in base 44 of the cusp.

FIG. 3A shows another embodiment of the cusp's terminus; here the tip is more salient than that shown in FIG. 3.

FIG. 3B shows another terminus wherein the tip is planar and provides a wide skin contact area.

FIG. 3C shows another version of the terminus which has a planar contacting area, but actually has a smaller area than that shown in 3B, but more than that shown in FIG. 3.

FIG. 3D shows a terminus with a rounded or hemispherical contact point.

FIG. 3E shows one with an angular contact area.

FIG. 4—DESCRIPTION

FIG. 4 shows a stimulator 46 in which tip 45 is attached by a threaded pin or stud 48 to a base 58. The flat top 60 of base 58 has several holes 50, 52, and 54 into which stud 48 can be mounted; these holes are provided at various locations and are drilled at various angles. Tip 45 has a cylindrical configuration, which alternatively can be conical. The length of the cusp can be effectively increased or decreased by variable rotation of stud 48 into one of holes 50, 52, or 54. For even greater variation in cusp length, different lengths of threaded studs may be employed, as illustrated by long stud 56.

FIG. 5—DESCRIPTION

FIG. 5 shows another embodiment of the stimulator which differs from that in FIG. 1 in that the cusp is conical, rather than angular.

FIG. 6—DESCRIPTION

FIG. 6 shows a stimulator in which a cusp portion 62 extends from the center of and is integral with base portion 64, rather than from one side as in FIG. 1. Holes are provided for applying pressure via the band at differing angles.

FIG. 7—DESCRIPTION

FIG. 7 shows another embodiment of the stimulator and indicates how the cusp may be made long with a narrow angular profile. Long cusp 66 is about 34 mm in height and its sides taper at an angle of about 30°. FIG. 7 also shows a relatively short radius curve or contoured side 68 to which the band is attached. At the other extreme, the cusp may be short and squat and the curved side may have a relatively large radius.

OPERATION AND USE

The first step in using my invention is to locate the acupoint. Acupoints are widely distributed over the body surface. Each point has a definite location which must be determined accurately for effective stimulation or therapeutic results. An authoritative book and/or chart of acupoints is needed to determine which points are associated with relieving a particular problem.

In *Acupuncture: A Comprehensive Text*, cited above, it is noted that when locating the exact position of an acupoint, the most important single guide is sensitivity. Generally, acupoints are found in depressions in the muscles or joints, and are often sensitive to finger pressure, particularly where an illness or symptom with which a certain point is associated is present in the body.

There are three commonly used methods for determining these locations:

(1) Location through recognition of body features or anatomical landmarks. These include prominence or depression of the bone, joint, tendon, muscle, skin crease, border of nail, nipple, umbilicus, etc.

(2) Location through proportional measurement. In this method a fixed number of units is assigned to the distance between two given body locations. This system of attributing a certain number of units of distance between two given body features is applicable to any person, regardless of size. These units are known as anatomical Chinese inches (ACI) acupuncture units of measurement (AUM), the Chinese word "cun", or simply "units."

(3) Location using finger measurement. When the middle finger is flexed, the distance between the two ends of the creases of the interphalangeal joints is taken as one cun. In other words, this is the distance between the wrinkles at the first and second joints of the middle finger.

The breadth of four fingers (excluding the thumb) placed side by side at the level of the distal joint is three units.

For illustrative purposes, the acupoint Spleen Six or Sanyinjiao will be located. Spleen Six is traditionally indicated for pain of the genitalia and lower extremities, incontinence, diseases of reproductive system, borborygmus, diarrhea, insomnia, irregular menstruation, eczema, uticaria, and enuresis. This is by no means an exhaustive list.

*Acupuncture and Moxibustion, A Handbook for the Barefoot Doctors of China,* translated by M. E. Silverstein, I. Chang, and N. Macon, Schocken Books, New York, 1975, shows that Sanyinjiao is located "on the inner surface of the leg above the inner ankle just behind the shin bone . . . . Holding the index, middle, and ring fingers together, press down in the depression above the ankle, behind the tibia on the inner surface to locate a cavity; this cavity is the point." In *Essentials of Chinese Acupuncture* the location of Spleen Six is given as "three cun directly above the tip of the medial malleolus, on the posterior border of the tibia."

These two texts provide two approaches to locate the point. As indicated, three cun is the breadth of four fingers. Thus, Spleen Six is four fingers, width above the highest point of the anklebone or three fingers, width (index, middle, and ring) above the depression superior to the anklebone. Palpating this small area with a fingertip will usually uncover a point of strong sensitivity.

The top of the cusp of the stimulator is placed on the acupoint, as shown in FIG. 2. Then the cinching strap is extended around the leg and secured in place. The strap is tightened to the degree that stimulation of the acupoint is felt, but not so much as to cause considerable discomfort or to inhibit blood circulation. The wearer should be able to walk around without difficulty. If walking causes discomfort, the band is too tight and should be loosened, maintaining the position of the tip on the acupoint.

By the use of the concave back on the stimulator, and the attachment of the cinching band at the center of the back, lateral or circumferential forces will not be applied to the stimulator once it is in position so that most of the force from the cinching band will be applied in an efficient, perpendicular direction, where it is needed. Also by use of the unilaterally-or asymmetrically protruding cusp and its ability to be positioned asymmetrically, symmetrically, or at any angle, almost any acupoint can be stimulated in any desired manner, conveniently, and scientifically. E.g., since the protrusion or cusp (22, 40, or 45) extends from one end of top or front surface 26 of the stimulator, it is unilaterally or asymmetrically positioned on such surface; this asymmetric location of the protrusion or cusp, together with the assymmetric position of the attachment point of band 10 on back or bottom surface 26 (when viewed from a direction perpendicular to the loop of band 10), enables the stimulator to be positioned so that it can apply non-perpendicular force. Thus it can stimulate an acupressure point behind a bone, such as the aforementioned acupressure point known as Spleen Six, which is at the posterior margin of the tibia (FIG. 2).

The length of time over which the stimulator should be worn also is variable with the individual. Some users find that the device can be worn with positive effects most of or all the day, even during sleep, while others prefer to wear the device for relatively short intermittent periods (10 min. to 1 hr.).

As has been noted, the amount of sensitivity and tenderness of the point is usually indicative of the extent of the problem it is treating. As the device presses the acupoint, the tension will tend to dissipate. Whether to tighten the band to effect more pressure on the point or to loosen it as the tension dissipates is a matter of personal preference. Some people find that lighter pressure at first followed by progressive tightening of the band is preferable. Others find the opposite to be true.

Likewise, the choice of tip composition, hardness, and shape is largely a matter of personal preference. Some people prefer light stimulation with an unyielding, rigid tip. Others prefer strong pressure with a soft, compressable tip.

Many of these considerations will depend upon the amount of body fat, musculature, and tension located at the particular acupoint targeted for stimulation. Also, the user's activities, for example whether lying supine or walking, may determine one's preference at that particular time.

It should be noted that the design of my invention includes provision for wide-ranging variability of pressure with the cinching strap. Even if the tip of the stimulator is rigid and unyielding, considerable control can be exercised over the amount of pressure exerted upon an acupoint.

While the above description contains many specificities, these should not be construed as limitations on the scope of my invention, but rather as an exemplification of one preferred embodiment thereof. Many other variations are possible. For example, FIG. 1 shows the stimulator attached to the band proximal to the rectangular ring to take advantage of unequal pressure exerted on the stimulator upon tightening of the band. This arrangement is useful for stimulation of Spleen Six. However, the stimulator attachment point could be moved, for example, to the center of the band if a particular acupoint would be more effectively stimulated that way. Also, the length of the band may be varied to facilitate use on a larger body part, for example to extend around a thigh or waist portion of a user's anatomy. Also the sides may be rounded and the dimensions of the band and stimulator are relative to the location of an acupoint and the most conducive means to stimulate said acupoint. Further, different compositions or types of substances may be used for all or part of the stimulator. Certain shapes, substances and colors are believed by some to have specific energetic characteristics. For example, pyramidal or conical shapes or crystal or jewelled or magnetized substances, in themselves, are believed by some to have beneficial effects or be able to channel, change, or emit certain energies. Thus, these may be effectively used for the cusp or the entire stimulator for their objective and/or subjective effects. Accordingly, the scope of the invention should be determined not by the embodiment illustrated, but by the appended claims and their legal equivalents.

What is claimed is:

1. An accupressure device for applying continuous pressure to a specific spot on an animal's body, comprising:

an elongated solid-body stimulator having front and back sides, said back side having a convex curvature, said front side being on the opposite side of said solid-body from said back side thereof and comprising a protuberance, the end of said protuberance distal from said back side having a terminus, said terminus being asymmetrically positioned on said front side toward one end of said elongated solid body, means for holding said solid-body stimulator against said animal's body so that said terminus of said protuberance is in contact with said specific spot thereon, said means arranged to apply continuous pressure to a symmetrically-positioned spot on said back side of said stimulator, whereby said stimulator can be positioned to apply pressure at an angle to said animal's body so that a point behind or on a posterior margin of a bone can be stimulated.

2. The device of claim 1 wherein said protuberance is removable and interchangeable.

3. The device of claim 2, further including a plurality of protuberances of different respective shapes and colors, and means for attaching each of said protuberances to the rest of said stimulator for separate respective use therewith.

4. The device of claim 1 wherein said protuberance is fabricated of a compressable and resilient material.

5. The device of claim 1, wherein said terminus of said protuberance is removable and interchangeable.

6. The device of claim 1 wherein both said elongated protuberance and said terminus thereof are interchangeable.

7. The device of claim 1 wherein said tip is comprised of a substantially noncompressible and nonresilient mineral material.

8. The device of claim 1 wherein said tip is comprised of a magnetized material.

9. The device of claim 1 wherein said front side of said stimulator body comprises a flat portion and said protuberance; said flat portion and said protuberance both being asymmetrically located on said front side thereof when said stimulator is seen in said viewing direction, said flat portion being closer to said specific spot on said back surface of said body than said terminus of said protuberance.

10. The device of claim 9 wherein said protuberance has a side adjoining said flat portion and extending at an acute angle from said flat portion.

11. An acupressure device comprising a solid body stimulator and a ho lding band, said band being sized and arranged to encircle said stimulator and a portion of an animal's body so as to hold said stimulator against said portion of said animal's body, said stimulator having a convex back side, said band forming a loop when it encircles said stimulator and said portion of said animal's body, said loop being parallel to a plane, said band having one portion thereof attached to said back side of said stimulator, said stimulator having a front side which comprises the opposite side of said stimulator from said back side, said front side comprising a protuberance which is asymmetrically positioned from the attachment of said band to said back side when said device is viewed in a given direction perpendicular to said plane of said loop, and said band being symmetrically positioned on said back side when said device is viewed parallel to said plane.

12. The device of claim 11 wherein said stimulator has two substantially flat side faces joining said front and back sides, and wherein, when said device is viewed in said given direction, said front side of said stimulator has a flat portion extending from one end thereof and said protuberance forms the rest of said front side and extends from the other end thereof such that said protuberance is asymmetrically positioned when viewed in said given direction.

13. The device of claim 11 wherein said back side of said stimulator is curved when traversed in the circumferential direction of said band around said loop and is flat when traversed in said given direction perpendicular to said plane of said loop.

14. The device of claim 13 wherein said stimulator has two substantially flat side faces joining said front and back sides and wherein, when said device is viewed in said given direction, said front side of said stimulator has a flat portion extending from one end thereof and said protuberance forms the rest of said front side and extends from the other end thereof such that said protuberance is asymmetrically positioned when viewed in said given direction.

15. The device of claim 14 wherein said band is attached to the center of said back side thereof.

16. The device of claim 14 wherein said protuberance has a side adjoining said flat portion and extending at an acute angle therefrom.

* * * * *